United States Patent
Nelson, Jr. et al.

(10) Patent No.: US 7,275,414 B2
(45) Date of Patent: Oct. 2, 2007

(54) EXTRACTIVE SAMPLING SYSTEM AND METHOD FOR MEASURING ONE OR MORE MOLECULAR SPECIES

(75) Inventors: David Dodge Nelson, Jr., North Chelmsford, MA (US); Scott Christopher Herndon, Littleton, MA (US); John Barry McManus, Arlington, MA (US); Mark Stuart Zahniser, Lexington, MA (US); Charles Eugene Kolb, Bedford, MA (US)

(73) Assignee: Aerodyne Research Inc., Billerica, MA (US)

( * ) Notice: Subject to any disclaimer, the term of this patent is extended or adjusted under 35 U.S.C. 154(b) by 0 days.

(21) Appl. No.: 11/269,588

(22) Filed: Nov. 9, 2005

(65) Prior Publication Data

US 2006/0096394 A1    May 11, 2006

Related U.S. Application Data (60) Provisional application No. 60/625,956, filed on Nov. 9, 2004.

(51) Int. Cl.
*G01N 7/00* (2006.01)
(52) U.S. Cl. .................. 73/23.31; 73/23.2; 73/31.03
(58) Field of Classification Search ............. 73/23.31, 73/23.2, 31.03
See application file for complete search history.

(56) References Cited

U.S. PATENT DOCUMENTS

| | | | | |
|---|---|---|---|---|
| 2,658,434 A | * | 11/1953 | Miller | .......................... 138/90 |
| 2,726,594 A | * | 12/1955 | Cooper et al. | .............. 454/167 |
| 3,439,527 A | * | 4/1969 | Rohrer | ..................... 73/40.5 A |
| 4,704,897 A | * | 11/1987 | Kawase et al. | .......... 73/40.5 R |
| 4,979,390 A | * | 12/1990 | Schupack et al. | .............. 73/38 |
| 5,046,353 A | * | 9/1991 | Thompson | ................... 73/40.7 |
| 5,210,702 A | | 5/1993 | Bishop et al. | .............. 364/496 |
| 5,291,265 A | | 3/1994 | Kebabian | ..................... 356/246 |
| 5,319,199 A | | 6/1994 | Stedman et al. | ......... 250/338.5 |
| 5,401,967 A | | 3/1995 | Stedman et al. | ......... 250/338.5 |
| 5,591,975 A | | 1/1997 | Jack et al. | ............... 250/338.5 |
| 5,726,450 A | | 3/1998 | Peterson et al. | ......... 250/338.5 |
| 5,797,682 A | | 8/1998 | Kert et al. | ................... 374/123 |
| 5,831,267 A | | 11/1998 | Jack et al. | ............... 250/338.5 |
| 5,877,862 A | | 3/1999 | Nelson et al. | .............. 356/436 |
| 2002/0194897 A1 | * | 12/2002 | Arnott et al. | .............. 73/23.31 |

OTHER PUBLICATIONS

Zahniser, Mark S., et al., "Measurement of Trace Gas Fluxes Using Tunable Diode Laser Spectroscopy", *Phil. Trans. R. Soc. Lond. A*, vol. 351, 1995, pp. 371-382.

(Continued)

*Primary Examiner*—Michael Cygan
(74) *Attorney, Agent, or Firm*—Pillsbury Winthrop Shaw Pittman, LLP (57) ABSTRACT

A non-contact, extractive sampling system and method is provided for measuring the exhaust gas composition and fine particle composition of exhaust emissions of various types of vehicles under actual operating conditions. A portion (or sample) of an exhaust plume of a vehicle is pulled or extracted through an extraction sampling tube, via a vacuum pump, to a remote trace gas detection system where the concentration of one or more constituents present in the sample of exhaust plume may be measured. In this regard, the invention enables vehicle emissions measurements to be made at a location remote from roadway, rather than using known, "cross-path" remote emissions sensing systems.

50 Claims, 6 Drawing Sheets

OTHER PUBLICATIONS

Nelson, David D., et al., "High Precision Measurements of Atmospheric Nitrous Oxide and Methane Using Thermoelectrically Cooled Mid-Infrared Quantum Cascade Lasers and Detectors", *Spectrochimica Acta Part A*, 2004, pp. 1-11.

Houghton, J. T., et al., "Climate Change 2001: The Scientific Basis", Contribution of Working Group I to the Third Assessment Report of the Intergovernmental Panel of Climate Change, First published 2001, pp. i-x.

The North American Carbon Program, NACP Committee of the U.S. Carbon Cycle Science Steering Group, 2002, pp. ii-v.

Nelson, D. D., et al., "Sub-Part-Per-Billion Detection of Nitric Oxide in Air Using a Thermoelectrically Cooled Mid-Infrared Quantum Cascade Laser Spectrometer", *Applied Physics B*, vol. 75, 2002, pp. 343-350.

Edwards, G. C., et al., "Eddy Correlation Measurements of Methane Fluxes Using a Tunable Diode Laser at the Kinosheo Lake Tower Site During the Northern Wetlands Study (NOWES)", *Journal of Geophysical Research*, vol. 99, No. D1, Jan. 20, 1994, pp. 1511-1517.

Wienhold, F. G., et al., "Measurements of $N_2O$ Fluxes from Fertilized Grassland Using a Fast Response Tunable Diode Laser Spectrometer", *Journal of Geophysical Research*, vol. 99, No. D8, Aug. 20, 1994, pp. 16,557-16,567.

Kosterev, Anatoliy A., et al., "Transportable Automated Ammonia Sensor Based on a Pulsed Thermoelectrically Cooled Quantum-Cascade Distributed Feedback Laser", *Applied Optics*, vol. 41, No. 3, Jan. 20, 2002, pp. 573-578.

Allan, David W., "Statistics of Atomic Frequency Standards", *Proceedings of the IEEE*, vol. 54, No. 2, Feb. 1966, pp. 221-230.

Hansen, James, et al., "Global Warming in the Twenty-First Century: An Alternative Scenario", *PNAS*, vol. 97, No. 18, Aug. 29, 2000, pp. 9875-9880.

Kormann, Robert, et al., "Eddy Flux Measurements of Methane Over the Fen 'Murnauer Moos', 11°11'E, 47°39'N, Using a Fast Tunable Diode Laser Spectrometer", *Atmospheric Environment*, vol. 35, 2001, pp. 2533-2544.

Werle, Peter, et al., "Fast Chemical Sensor for Eddy-Correlation Measurements of Methane Emissions from Rice Paddy Fields", *Applied Optics*, vol. 40, No. 6, Feb. 20, 2001, pp. 846-858.

McManus, J. Barry, et al., "Quantum Cascade Lasers for Open and Closed Path Measurement of Atmospheric Trace Gases", *SPIE*, 2002, Aerodyne Research, Inc., 12 pages.

Jimenez, J. L., et al., "Cross Road and Mobile Tunable Infrared Laser Measurements of Nitrous Oxide Emissions from Motor Vehicles", *Chemosphere—Global Change Science*, vol. 2, 2000, pp. 397-412.

Rothman, L. S., et al., "The HITRAN Molecular Spectroscopic Database: Edition of 2000 Including Updates Through 2001", *Journal of Quantitative Spectroscopy & Radiative Transfer*, 2003, pp. 1-39.

McManus, J. B., et al., "Astigmatic Mirror Multipass Absorption Cells for Long-Path-Length Spectroscopy", *Applied Optics*, 1994, 14 pages.

Sonnenfroh, David M., et al., "Application of Balanced Detection to Absorption Measurements of Trace Gases with Room-Temperature, Quasi-cw Quantum-Cascade Lasers", *Applied Optics*, vol. 40, No. 6, Feb. 20, 2001, pp. 812-820.

Werle, P., et al., "The Limits of Signal Averaging in Atmospheric Trace-Gas Monitoring by Tunable Diode-Laser Absorption Spectroscopy (TDLAS)", *Applied Physics B*, vol. 57, 1993, pp. 131-139.

Kosterev, Anatoliy A., et al., "Trace-Gas Detection in Ambient Air with a Thermoelectrically Cooled, Pulsed Quantum-Cascade Distributed Feedback Laser", *Applied Optics*, vol. 39, No. 36, Dec. 20, 2000, pp. 6866-6872.

Faist, J., et al., "Sensitive Absorption Spectroscopy with a Room-Temperature Distributed-Feedback Quantum-Cascade Laser", *Optics Letters*, vol. 23, No. 3, Feb. 1, 1998, pp. 219-221.

Kelly, Kerry, et al., "Black Carbon and Polycyclic Aromatic Hydrocarbon Emissions from Vehicles in the United States-Mexico Border Region: Pilot Study", Technical Paper, *Journal of the Air & Water Management Association*, vol. 56, Mar. 2006, pp. 285-293.

Kurniawan, A., et al., "Monitoring the Soot Emissions of Passing Cars", *Environmental Science & Technology*, vol. 40, No. 6, 2006, pp. 1911-1915.

\* cited by examiner

EXTRACTIVE SAMPLING SYSTEM AND METHOD FOR MEASURING ONE OR MORE MOLECULAR SPECIES

CROSS-REFERENCE TO RELATED APPLICATIONS

This Application claims priority to U.S. Provisional Patent Application Ser. No. 60/625,956, filed Nov. 9, 2004, which is hereby incorporated herein by reference in its entirety.

STATEMENT REGARDING FEDERALLY SPONSORED RESEARCH OR DEVELOPMENT

This invention was made with U.S. Government support under Contract No. 68-D-00-270, awarded by the Environmental Protection Agency. The U.S. Government has certain rights in this invention.

FIELD OF THE INVENTION

The invention relates generally to the measurement of one or more molecular species, and more particularly to a non-contact, extractive sampling system and method for measuring the exhaust gas composition and fine particle composition of exhaust emissions of various types of vehicles under actual operating conditions.

BACKGROUND OF THE INVENTION

Systems and methods for monitoring the exhaust gas composition and fine particle composition of exhaust emissions of various types of vehicles are known. For example, with regard to automobiles, it is common for emissions inspection stations (or automotive repair facilities) to utilize dynamometers for controlled engine loading tests for the purposes of exhaust emission measurement. One drawback associated with dynamometer testing, however, is that the measurements acquired often do not represent emissions under actual operating conditions when automobiles are in motion on a roadway or other driving surface.

To remedy these and other drawbacks associated with dynamometer testing, remote emissions sensing systems have been developed to remotely monitor the exhaust gas composition of automobiles traveling past "test sites" located along streets or highways. Examples of remote emissions sensing (or "cross-road") systems are described in, for example, U.S. Pat. Nos. 5,210,702, 5,319,199, 5,401,967, 5,591,975, 5,726,450, 5,797,682, 5,831,267, and 5,877,862, each of which is hereby incorporated herein by reference in its entirety.

Despite steady advances in the sophistication and robustness of remote emissions sensing systems, the implementation of some such systems may be somewhat time and/or labor intensive. For example, the equipment comprising a remote emissions sensing system is often transported to a test site in a vehicle (e.g., a van), assembled for a testing session, calibrated, disassembled after the testing session, and either transported to a new test site or returned to a central facility where acquired emissions (and other) data may be processed.

Moreover, some remote emissions sensing systems remain susceptible to erroneous readings or inconsistent results. Unfortunately, such drawbacks can sometimes lead to relatively high incidences of discarded data or relatively high incidences of "flagged" test results, which indicate suspect results.

In addition, existing remote emissions sensing systems often utilize external mirrors to direct light beams through vehicle plumes. These exposed mirrors require careful alignment and are subject to alignment drift, degradation from the elements, and/or vandalism. This may present difficulties when deploying such systems without an operator, or when deploying them under adverse weather conditions.

Additionally, existing remote sensing systems can be limited in the number of molecular species that they can monitor with sufficient sensitivity, and in the type of detailed particulate information that they can provide. Current commercial instruments monitor only a few molecular species which typically do not include "air toxics" like formaldehyde, acrolein and 1,3-butadiene. Also, some of these monitors provide only an opacity measurement for particles. An opacity measurement provides little or no information regarding the size distributions or chemical compositions of particulate matter.

These and other problems can reduce the benefits of remote emissions sensing systems.

SUMMARY OF THE INVENTION

The invention addressing these and other drawbacks in the art relates to a non-contact, extractive sampling system and method for measuring the concentration of one or more constituents present in a gas sample. Although the various embodiments of the invention will be described herein with reference to the extractive sampling of exhaust emissions from one or more vehicles (e.g., automobiles) traveling on a roadway, it should be understood that the system and method of the invention are applicable to any type of emissions-producing vehicle traveling under actual (or simulated) operating conditions.

According to an embodiment of the invention, to measure the emissions of vehicles traveling on a roadway, a portion of an extraction sampling tube or series of tubes may be placed across the surface of the roadway such that an end of each sampling tube is positioned approximately in or near the center of a vehicle travel lane on the roadway. A sample of an exhaust plume from a passing vehicle may be drawn through the sampling tube, via a vacuum pump, to a trace gas detection system located remotely from the roadway. The trace gas detection system may measure the concentration of one or more constituents present in the sample of the exhaust plume. Generally, a major gaseous exhaust species (e.g., $CO_2$ or $H_2O$ vapor) will be measured along with selected minor pollutant gases or fine particles so that emission indices for the minor exhaust gases and fine particles can be deduced.

The probability of acquiring a high number of suitable exhaust plume samples for valid measurements may be greater when the end of a sampling tube is positioned approximately in or near the center of a vehicle travel lane on a roadway rather than, for example, on the side of the roadway. Placing the end of the sampling tube in the center of a vehicle travel lane on a roadway enables the sampling tube to catch emissions from passing vehicle regardless of whether their exhaust pipes are mounted on the left side, right side, or on both sides (e.g., dual exhaust pipes) of the vehicle.

Additionally, it should be appreciated that exhaust leaving the exhaust pipe of a moving vehicle is entrained in the turbulent wake of the vehicle and gradually dissipates as the vehicle travels away. A turbulent exhaust wake generally ensures that a portion of the exhaust plume may reach the surface of the roadway where it can be drawn into the end of the sampling tube. Since the exhaust pipes of most low-emitter vehicles are positioned approximately one foot above the ground, the distance between the end of a sampling tube (placed in the center of a roadway) and the exhaust pipe of a passing vehicle is typically two to three feet and may be as little as one foot if the exhaust pipe passes directly over the end of sampling tube. This close proximity between the end of the sampling tube and the exhaust pipe and the location of the end of the sampling tube below the exhaust pipe enables exhaust plume samples to be efficiently acquired under almost any wind conditions, as it is the wake of the vehicle that serves to deliver a portion of the exhaust plume to the end of the sampling tube.

According to one embodiment of the invention, a vacuum pump may be configured to continuously or periodically sample air at a predetermined flow rate from the end of the sampling tube positioned in the roadway. As a vehicle passes by the sampling tube, a sample of the vehicle's exhaust plume may be drawn through the sampling tube toward the trace gas detection system. As the vacuum pump draws the exhaust plume sample away from the roadway, the pressure in the sampling tube may decrease from atmospheric pressure at the end of the sampling tube positioned in the roadway, to a predetermined pressure level at a measurement space or cell where the concentration of one or more constituents present in the exhaust plume sample may be measured.

Characteristics of the sampling tube (e.g., length, diameter, cross-section, etc.), and/or operating parameters of the vacuum pump may be adjusted as necessary to achieve desired flow rates and pressure drops within the sampling tube. Such adjustments to these and other components of the system may ensure that optimal conditions exist for measuring the concentration of one or more constituents present in an exhaust plume sample. Optimal conditions may vary depending on which molecular species of interest are being measured, as well as which type of trace gas detection system is being implemented to best measure the molecular species of interest.

According to an embodiment of the invention, the trace gas detection system may comprise any system capable of measuring the concentration of one or more constituents of an exhaust gas sample introduced in a measurement space or cell (via the sampling tube and vacuum pump). For instance, the trace gas detection system may comprise a mass spectrometer, visible/ultraviolet absorption spectrometer, infrared absorption spectrometer, or other known or subsequently developed trace gas detection instrument or system. The fine particle measurement system may comprise an aerosol mass spectrometer, condensation particle counter, light scattering detector, laser incandescent particle detector or other known or subsequently developed fast response, fine particle instrument or system.

In one implementation, the trace gas detection system may comprise a Quantum Cascade (QC) Tunable Infrared Laser Differential Absorption Spectrometer (TILDAS), and the measurement cell may comprise a multipass cell such as, for example, an astigmatic multipass absorption cell offered commercially by Aerodyne Research, Inc., and as disclosed in U.S. Pat. No. 5,291,265, which is hereby incorporated herein by reference in its entirety.

The system and method of the invention as disclosed herein may be utilized to measure emissions from a plurality of vehicles over a predetermined period of time (e.g., emissions attributable to general traffic). Additionally, however, the system and method of the invention may be configured to associate individual exhaust samples with individual vehicles. In this instance, a calibration procedure may be implemented to calculate the time delay from when a calibration sample (e.g., a puff of $CO_2$ or other gas) enters the end of the sampling tube on the roadway, until it reaches the trace gas detection system for measurement. The time delay may vary depending on the length and/or diameter of the sampling tube, the strength of the vacuum pump, or other factors.

According to an embodiment of the invention, for a given test period, a computer (or processor) may utilize the calculated time delay to correlate a record (or data file) of emissions measurements with a record of vehicles that have passed by the sampling tube during the test period. Both the measurements record and vehicle record may be stored in a memory associated with, or accessible by, the computer. Data regarding the identification of those vehicles passing by or over the sampling tube during the test period may be acquired by an imaging unit or other known identification device or system in operative communication with the computer (e.g., via a wireless or hard-wired connection). Other vehicle identification systems may be implemented.

These and other objects, features, and advantages of the invention will be apparent through the detailed description of the preferred embodiments and the drawings attached hereto. It is also to be understood that both the foregoing general description and the following detailed description are exemplary and not restrictive of the scope of the invention.

DETAILED DESCRIPTION OF THE INVENTION

Figure 1:
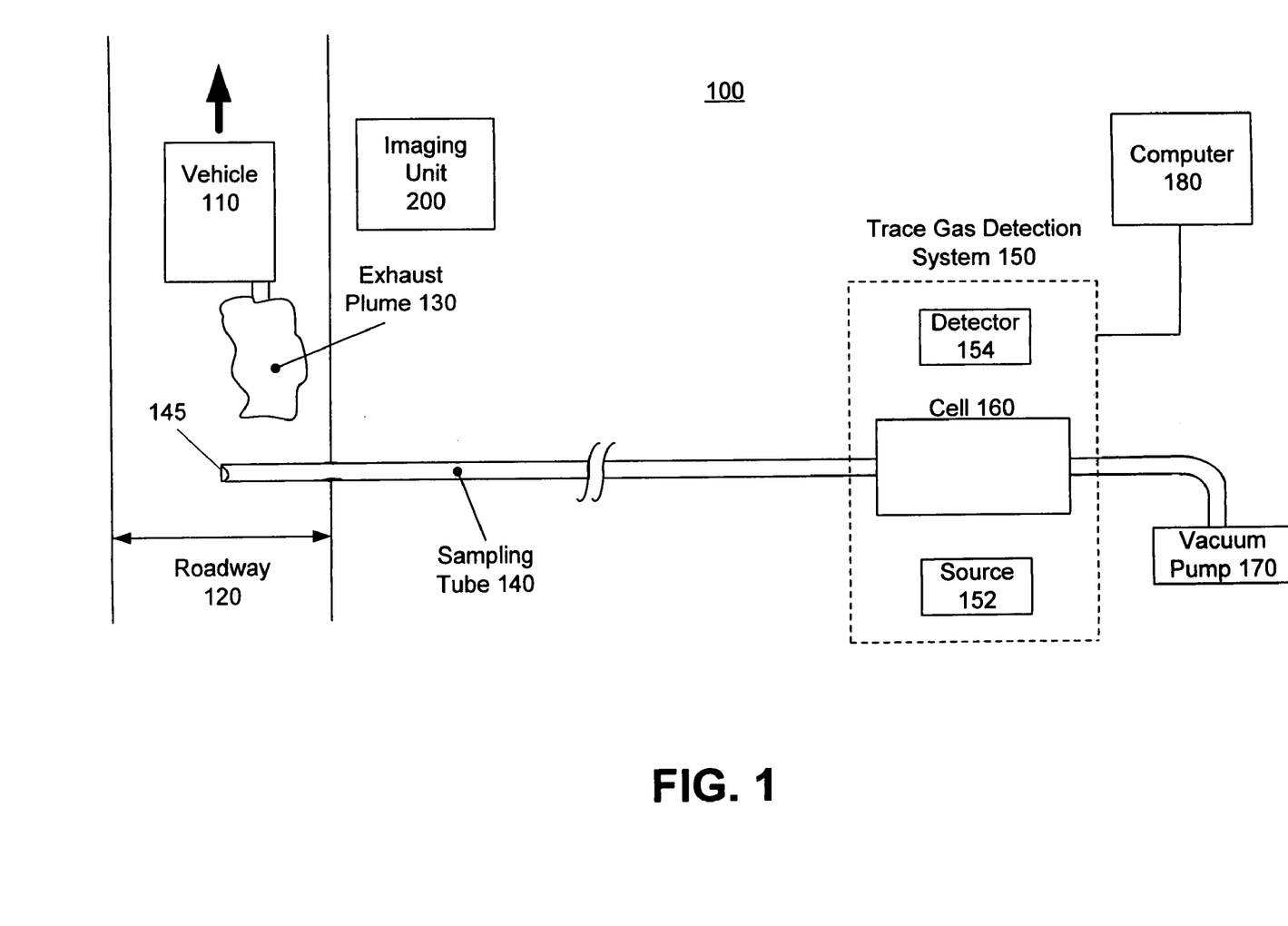
FIG. 1 is a schematic diagram of an extractive sampling system for measuring the exhaust gas composition and/or fine particle composition of exhaust emissions various types of vehicles under actual operating conditions.

According to an embodiment of the invention illustrated in FIG. 1, a system 100 is provided for measuring the concentration of one or more constituents present in an exhaust plume 130 of a low-emitter vehicle 110 traveling on a roadway 120, under actual operating conditions. Roadway 120 may comprise any driving surface suitable for the safe passage of vehicle 110, and may further comprise a single vehicle travel lane, or multiple vehicle travel lanes (e.g., one or more vehicle travel lanes in the same and/or opposite directions).

As will be discussed in greater detail herein, a portion (or sample) of exhaust plume 130 may be pulled or extracted through extraction sampling tube 140, via a vacuum pump 170, to a remote trace gas detection system 150 where the concentration of one or more constituents present in the sample of exhaust plume 130 may be measured. In this regard, the invention enables vehicle emissions measurements to be made at a location remote from roadway 120, rather than using known "cross-path" remote emissions sensing systems.

Figure 2:
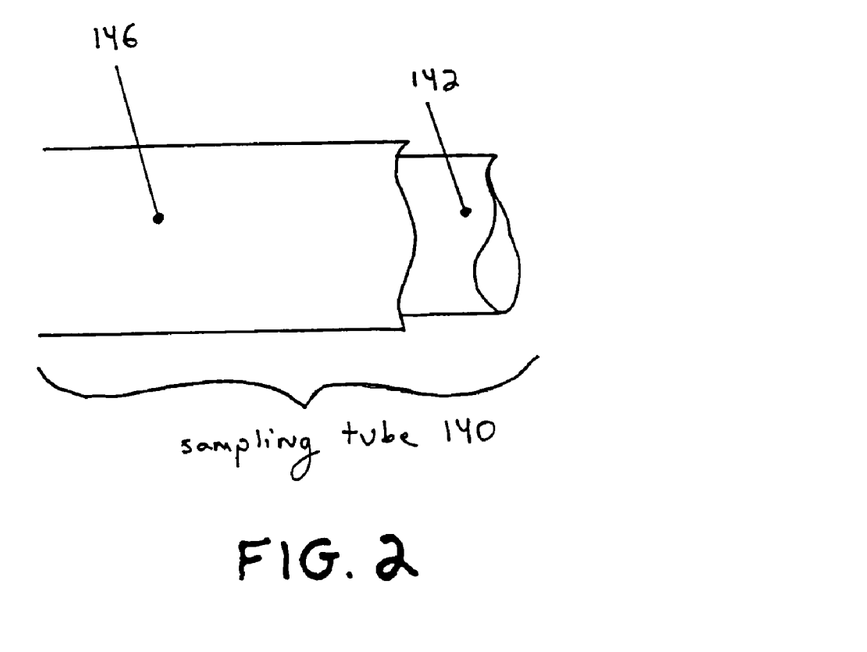
FIG. 2 is an exemplary illustration of an exposed section of an extraction sampling tube, according to an embodiment of the invention.

As depicted in FIG. 2, sampling tube 140 may comprise an inner tube 142 disposed within a protective outer tube 146. Inner tube 142 may be utilized to transport exhaust plume samples from roadway 120 to trace gas detection system 150, and may be fabricated from teflon, plastic, or other materials. Protective outer tube 146 may protect inner tube 142 from damage or destruction resulting from the weight of one or more vehicles driving over sampling tube 140. As such, protective outer tube 146 may be fabricated from any number of rigid, durable materials (e.g., copper or stainless steel), and may have an outer diameter of approximately ¼ inch. Tubes of other diameters may be used.

Figure 3A:
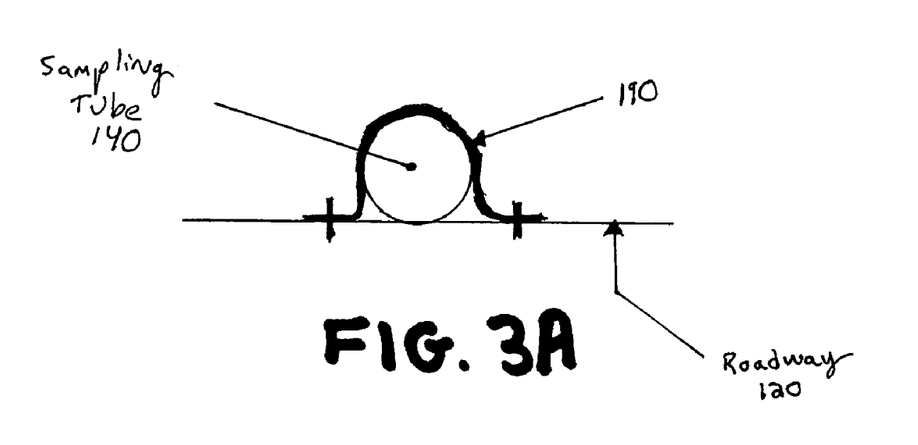
FIG. 3A is an exemplary illustration of an extraction sampling tube secured to the surface of a roadway, according to an embodiment of the invention.

According to an embodiment of the invention, a portion of sampling tube 140 may be run across the surface of roadway 120 such that the opening at a first end 145 of sampling tube 140 is positioned approximately in or near the center of a vehicle travel lane on roadway 120. Although other sampling tube placements may be contemplated, as described below, placing the first end 145 of sampling tube 140 approximately in or near the center of a vehicle travel lane on roadway 120 enables sampling tube 140 to catch emissions from passing vehicle regardless of whether their exhaust pipes are mounted on the left side, right side, or on both sides (e.g., dual exhaust pipes) of the vehicle. In some embodiments, the portion of sampling tube 140 that is run across the surface of roadway 120 may be secured to roadway 120 to keep sampling tube 140 in a fixed position. As illustrated in FIG. 3A, one or more brackets 190 or other known or subsequently developed fastening mechanisms may be used to secure sampling tube 140 to the surface of roadway 120.

It should be appreciated that exhaust leaving the exhaust pipe of a moving vehicle is entrained in the vehicle's turbulent wake and continues to dissipate as the vehicle travels away. A turbulent exhaust wake generally ensures that exhaust plume 130 may reach the surface of roadway 120 where it can be sucked into the first end 145 of sampling tube 140. This ensures that trace gas detection system 150 receives suitable exhaust plume samples for valid measurements.

Figure 3B:
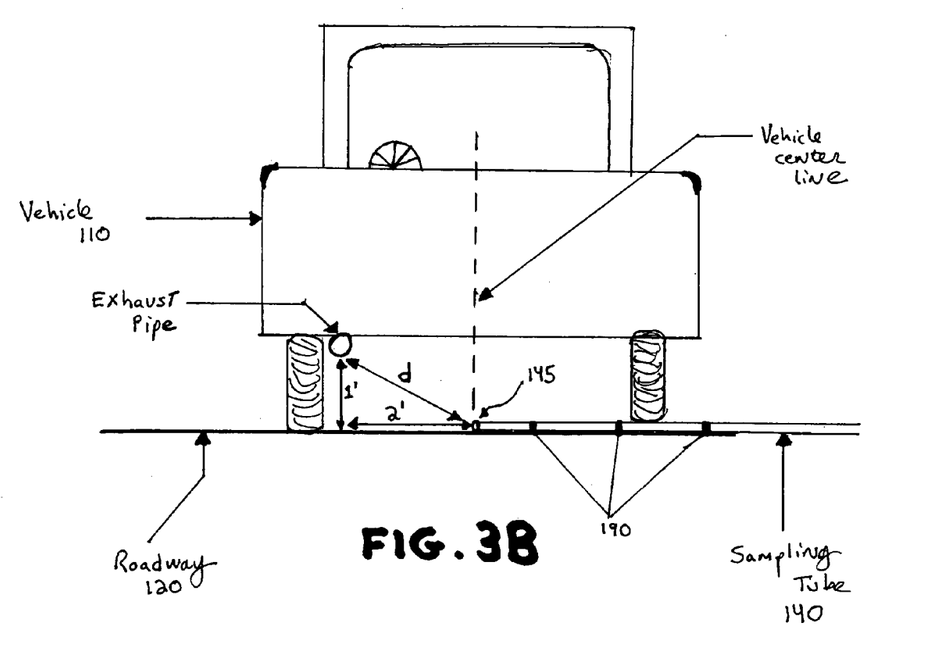
FIG. 3B is an exemplary illustration of a vehicle traveling over an extraction sampling tube, according to an embodiment of the invention.

In this regard, and with reference to FIG. 3B, the probability of acquiring a high number of exhaust plume samples may be greater with the first end 145 of sampling tube 140 positioned approximately in or near the center of a vehicle travel lane on roadway 120 rather than, for example, on the side of a vehicle travel lane on roadway 120. One reason for this finding is that the exhaust pipes of most low-emitter vehicles are positioned approximately one foot above the ground. Accordingly, the distance between sampling tube 140 and the exhaust pipe of passing vehicle 110 may be as little as one foot if the exhaust pipe passes directly over the first end 145 of sampling tube 140.

A more typical distance between the first end 145 of sampling tube 140 and the exhaust pipe may be two to three feet if the vehicle is centered in a travel lane on roadway 120 since the exhaust pipes of many vehicles (e.g., passenger vehicles) are offset from the vehicle center line by approximately two feet. This close proximity between the first end 145 of sampling tube 140 and the vehicle exhaust pipe and the location of the first end 145 of sampling tube 140 below the exhaust pipe enables exhaust plume samples to be efficiently acquired under almost any wind conditions (including a complete lack thereof), as it is the wake of vehicle 110 that serves to deliver a portion of exhaust plume 130 to the first end 145 of sampling tube 140.

By contrast, should the first end 145 of sampling tube 140 be positioned on the side of a vehicle travel lane of roadway 120, there will likely be a greater distance (e.g., as much as five or more feet) between sampling tube 140 and the exhaust pipe of passing vehicle 110. Accordingly, in such a scenario, it may be necessary to have a wind blowing across roadway 120 toward the first end 145 of sampling tube 140 in order to acquire a sample of exhaust plume 130. Reliance on an uncertain external factor such as the wind is disadvantageous.

According to one embodiment of the invention, vacuum pump 170 may be configured to continuously sample air at a predetermined flow rate (e.g., 5.0 standard liters per minute) from the first end 145 of sampling tube 140 positioned in roadway 120. As vehicle 110 passes by sampling tube 140, a "plug" of air including a sample of exhaust plume 130 may be drawn through sampling tube 140 toward trace gas detection system 150. The second end of sampling tube 140 interfaces (or is in operative contact) with a measurement cell 160 of trace gas detection system 150. The plug of air including the exhaust sample remains essentially intact with minimal spreading as it travels through sampling tube 140. The length of sampling tube 140 may differ in various system configurations as the distance between roadway 120 and trace gas detection system 150 differs. In some implementations, for example, sampling tube 140 may extend (approximately) as many as 100 meters in length, thus enabling trace gas detection system 150 to be located remotely from roadway 120.

The first end 145 of sampling tube 140, positioned on roadway 120, is at atmospheric pressure. As vacuum pump 170 draws the exhaust plume sample away from roadway 120 toward trace gas detection system 150, the pressure in sampling tube 140 may decrease to a predetermined pressure level, at measurement cell 160, where the concentration of one or more constituents present in the exhaust plume sample may be measured. In some embodiments, for instance, the pressure in sampling tube 140 may decrease to approximately 50 torr at measurement cell 160.

In various embodiments, characteristics of sampling tube 140 (e.g., length, diameter, cross-section, etc.), and/or operating parameters of vacuum pump 170 may be adjusted as necessary to achieve desired flow rates and pressure drops within sampling tube 140. Such adjustments to these and other components of system 100 may ensure that optimal conditions exist for measuring the concentration of one or more constituents present in an exhaust plume sample. Optimal conditions may vary depending on which molecular species of interest are being measured, as well as which type of trace gas detection system 150 is being implemented to best measure the molecular species or particle properties of interest.

Figure 4:
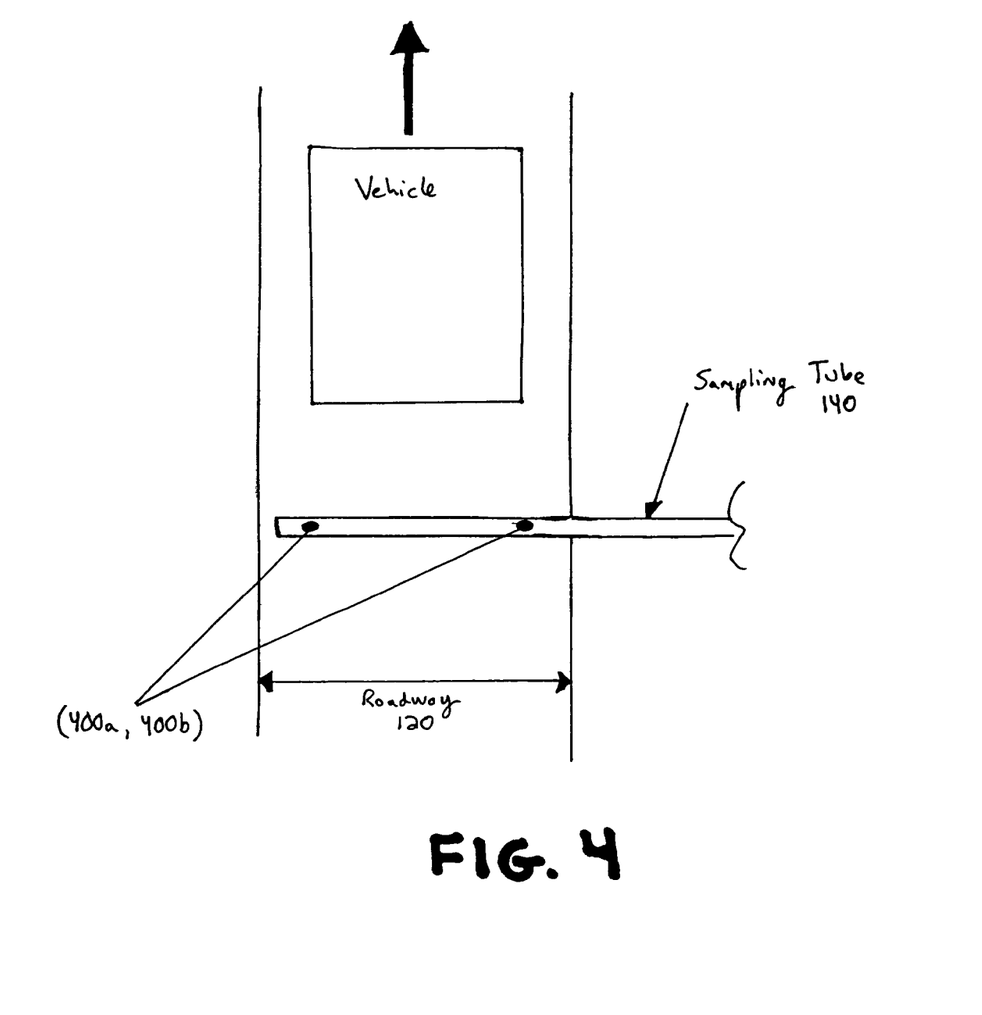
FIG. 4 is an exemplary illustration of an extraction sampling tube with multiple sampling points, according to an embodiment of the invention.

One embodiment of the invention may include a sampling tube (or tubes) having multiple sampling points for extracting exhaust gas samples from multiple locations on a roadway or other driving surface. For example, as illustrated in FIG. 4, sampling tube 140 may comprise two holes (400a, 400b) positioned to sample near the edges of (a vehicle travel lane on) roadway 120 since most vehicles have their exhaust pipes located off-center (e.g., either on the right or left side of the vehicle).

Figure 5:
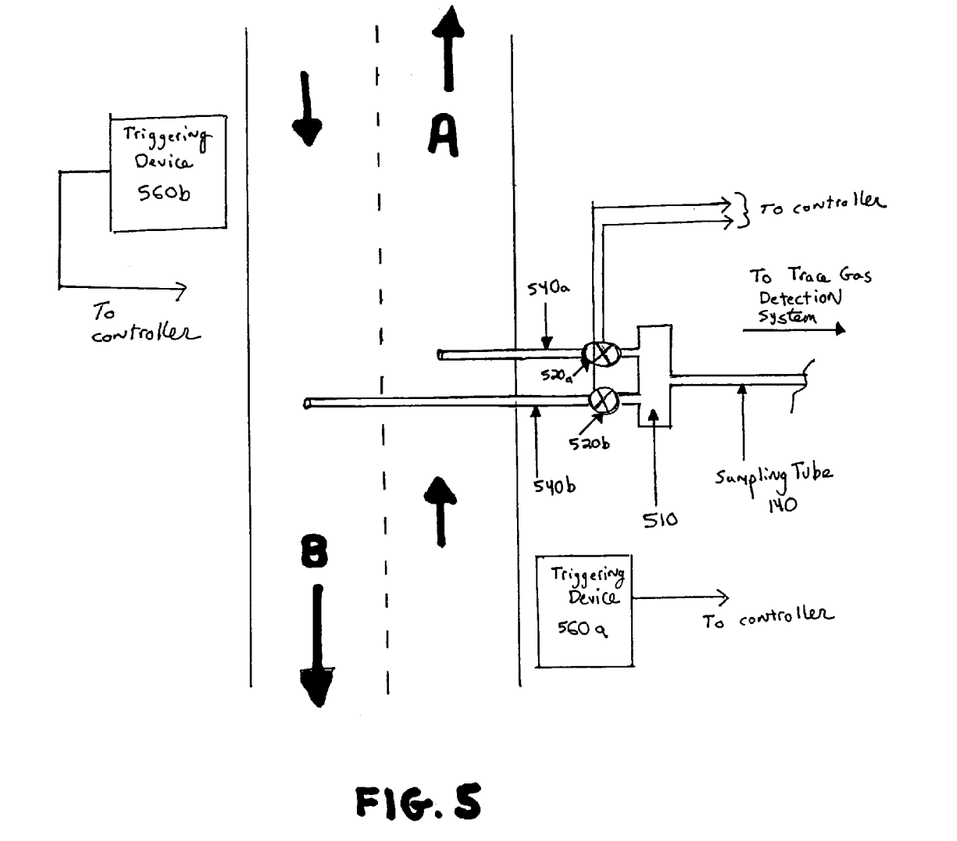
FIG. 5 is an exemplary illustration of multiple extraction sampling tubes present on a multilane roadway, according to an embodiment of the invention.

According to an alternative embodiment, illustrated in FIG. 5, the system and method of the invention may be implemented in a multilane environment (e.g., vehicle travel lane "A" in a first direction and vehicle travel lane "B" in a second, opposite direction), wherein a separate sampling tube (540a, 540b) may be provided for each travel lane ("A," "B") on a multilane roadway. Each sampling tube (540a, 540b) may be connected to a manifold 510, and electronic valves (520a, 520b) may be utilized to select a sampling tube (540a, 540b) corresponding to a particular lane ("A," "B") for sampling. One or more triggering devices (560a, 560b) may be positioned in or near each lane ("A," "B") to detect approaching vehicles such that the appropriate lane ("A," "B") and corresponding sampling tube (540a, 540b) is selected for sampling. The one or more triggering devices (560a, 560b) may comprise, for example, infrared motion sensors, pressure sensors, or other known or subsequently developed sensors capable of detecting an approaching vehicle.

In one implementation, each electronic valve (520a, 520b) and triggering device (560a, 560b) may have its own controller, and each controller may be in operative communication with one another. In another implementation, each electronic valve (520a, 520b) and triggering device (560a, 560b) may be in operative communication with (and controlled by) a computer 180 (FIG. 1) (e.g., via a wireless or hard-wired connection). Additional configurations may be implemented.

According to an embodiment of the invention, trace gas detection system 150 may comprise any system capable of measuring the concentration of one or more constituents of an exhaust gas sample introduced in a measurement space or cell 160 (via sampling tube 140 and vacuum pump 170). For instance, trace gas detection system 150 may comprise a mass spectrometer, visible/ultraviolet absorption spectrometer, infrared absorption spectrometer, or other known or subsequently developed trace gas detection instrument or system. The fine particle measurement system may comprise an aerosol mass spectrometer, condensation particle counter, light scattering detector, laser incandescent particle detector or other known or subsequently developed fast response, fine particle instrument or system.

According to one embodiment, trace gas detection system 150 may comprise a Quantum Cascade laser spectrometer (QC-TILDAS), wherein a source 152 may comprise a thermoelectrically cooled mid-infrared quantum cascade laser, and a detector 154 may comprise a thermoelectrically cooled mid-infrared detector. The lasers may be selected to operate at wavelengths absorbed by molecular species of interest (e.g., HC, CO, $CO_2$, $CH_4$, HCHO, acrolein, 1,3-butadiene, benzene, NO, $NO_2$, $N_2O$, $NH_3$, etc.). In this embodiment, measurement cell 160 may comprise a multipass cell such as, for example, an astigmatic multipass absorption cell offered commercially by Aerodyne Research, Inc., and as disclosed in U.S. Pat. No. 5,291,265, which is hereby incorporated herein by reference in its entirety. Other cells may be utilized. An example of a QC laser spectrometer system may be found in a reference entitled: "High Precision Measurements of Atmospheric Nitrous Oxide and Methane Using Thermoelectrically Cooled Mid-Infrared Quantum Cascade Lasers and Detectors," David D. Nelson et al., Spectrochemica Acta Part A, 60, 3437-3447 (2004), which is hereby incorporated herein by reference in its entirety. Such a TILDAS trace gas detector is advantageous for use with the extractive sampling system and method described herein, since the TILDAS method has improved sensitivity and specificity when applied to a sample at a reduced pressure level.

Figure 6:
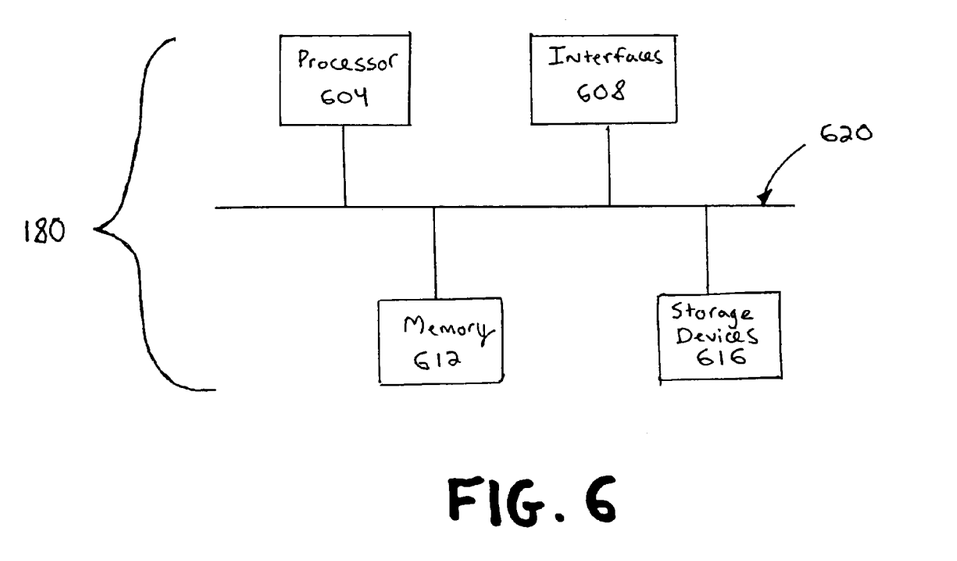
FIG. 6 is a schematic block diagram of a computer, according to an embodiment of the invention.

According to one aspect of the invention, computer 180 (FIG. 1) may be in operative communication with and/or control one or more components of trace gas detection system 150, vacuum pump 170, imaging unit 200 (described in detail below), or other components. For example, computer 180 may control a data acquisition (or sampling) session, as well as process and store data from trace gas detection system 150. Computer 180 may comprise a personal computer, portable computer (e.g., laptop computer), processor, or other device. As shown in FIG. 6, computer 180 may comprise a processor 604, interfaces 608, memory 612, and storage devices 616 which are electrically coupled via bus 620. Memory 612 may comprise random access memory (RAM), read only memory (ROM), or other memory. Memory 612 may store computer-executable instructions to be executed by processor 604 as well as data which may be manipulated by processor 604. Storage devices 616 may comprise floppy disks, hard disks, optical disks, tapes, or other known storage devices for storing computer-executable instructions and/or data. Interfaces 608 may comprise interfaces to various peripheral devices (e.g., keyboard, mouse, microphones, external storage devices, monitors, printers or other input and/or output devices as would be appreciated by those having skill in the art) as well as other components as described herein.

According to one aspect of the invention, computer 180 may be connected to a network (e.g., Internet, Intranet, etc.) so that emissions data or other information may be made accessible via a web site or other application (or transmitted a predetermined interval) to vehicle owners or operators, regulatory bodies (e.g., Dept. of Motor Vehicles), or to other entities.

In one embodiment of the invention, system 100 (FIG. 1) may be utilized to measure emissions from a plurality of vehicles over a predetermined period of time (e.g., emissions attributable to general traffic). Alternatively, system 100 may associate individual exhaust samples with individual vehicles. In this instance, a calibration procedure may be implemented to calculate the time delay from when a calibration sample (e.g., a puff of $CO_2$ or other gas) enters the first end 145 of sampling tube 140 on roadway 120, until it reaches cell 160 for measurement. The time delay may vary depending on the length and/or diameter of sampling tube 140, the strength of vacuum pump 170, or other factors.

According to an embodiment of the invention, for a given test period, computer 180 may utilize the calculated time delay to correlate a record (or data file) of emissions measurements with a record of vehicles that have passed by sampling tube 140 during the test period. Both the measurements record and vehicle record may be stored in a memory associated with, or accessible by, computer 180.

Data regarding the identification of those vehicles passing by sampling tube 140 during the test period may be acquired by an imaging unit 200 (FIG. 1) or other known identification device or system (not illustrated) in operative communication with computer 180 (e.g., via a wireless or hard-wired connection). Imaging unit 200 may comprise, for example, a film camera, video camera, or digital camera. Other imaging devices may also be used. Preferably, the imaging unit may record an image of the identification tag (e.g., license plate) of vehicle 110. Tag information may be processed by computer 180 to provide additional information about vehicle 110. For example, Motor Vehicle Department databases may be accessed to retrieve owner information, make, model type, model year, or other information.

According to one embodiment of the invention, an identification tag on vehicle 110 may be read to identify the vehicle and associate particular sensed vehicle emission information with the vehicle. An identification tag (defined as a license plate above), may also comprise a transponder located on or within vehicle 110 (e.g., hung from a rear view mirror, placed on the dashboard, etc.), or that is integral within the vehicle (e.g., part of a global positioning system ("GPS"), located within the engine of the vehicle, or placed or mounted elsewhere). The transponder may transmit information about vehicle 110, including make and model of vehicle 110, engine characteristics, fuel type, the owner of vehicle 110, or other information which may be pertinent. According to an embodiment of the invention, a transponder may be used in connection with other functions. By way of example, a transponder may also be used in connection with a toll pass, whereby a driver can electronically pay tolls via the transponder without stopping the vehicle.

An identification tag may also comprise a tag or decal that requires a reader. By way of example, an identification tag may comprise a decal with identifying marks (e.g., bar codes, infrared markings, etc.) containing information about vehicle 110. The decal may be located outside vehicle 110, such as on a front or rear bumper, on the under-side of vehicle 110, or any other location on vehicle 110 where the decal may be suitably read. A reader may observe the decal and thereby obtain information about vehicle 110.

A receiver may be used to obtain information form an identification tag. According to an embodiment of the invention, an antenna may receive signals transmitted from an identification tag containing a transponder. Any type of conventional receiver may be used to receive signals. According to an embodiment of the invention, one reader and/or receiver may be used in connection with multiple lanes. Based on the signal received or the decal read, a receiver or reader may determine in which lane a particular vehicle is located at a particular time.

Computer 180 may receive information about vehicle 110 from a reader and/or receiver. Vehicle information and information obtained by sensing vehicle emissions may be stored. Computer 180 may correlate vehicle information received from an identification tag with the results from vehicle emissions sensing. Computer 180 may update a vehicle record to include results obtained by processing vehicle emission data, such as information regarding whether a vehicle has passed or failed predetermined emissions criteria. Other vehicle identification systems may be implemented.

As recited above, the system and method of the invention are applicable to any type of emissions-producing vehicle traveling under actual operating conditions. As such, it should be understood that vehicle 110 may comprise any type of emissions-producing vehicle including, but not limited to, an automobile, a heavy-duty vehicle (e.g., truck, bus, etc.), an all-terrain vehicle (ATV) or other "off-road" vehicle (e.g., a snowmobile), a powerboat, a helicopter or airplane, train, or other vehicle.

Accordingly, in alternative embodiments, roadway 120 may be broadly interpreted as a "pathway" comprising any land, air, or waterway through or over which vehicle 110 may travel under various operating conditions. In addition to a roadway, the pathway may comprise an off-road path or trail, an aircraft runway, a portion of a lake, river, or other waterway designated for motor boat traffic, or even a designated airspace proximate to a helicopter pad, or airplane runway.

In various embodiments, the configuration or placement of sampling tube 140 may depend in part on the type of vehicle 110 being tested, the location on vehicle 110 where emissions are introduced into the environment, and the pathway being used. For example, if vehicle 110 comprises a truck or bus with high-stack emissions, sampling tube 140 may be placed at an elevated position such as, for instance, on an overpass or other structure (e.g., an elevated platform, scaffolding, or other structure).

Alternatively, if vehicle 110 comprises a powerboat, an end 145 (or other portion) of sampling tube 140 may extend off an elevated dock, pier, or other structure such that it is optimally positioned to receive emissions from a motor (e.g., an outboard motor) of the powerboat as the powerboat passes through, for example, a portion of a body of water marked off for testing with buoys.

Moreover, should vehicle 110 comprise an airplane or helicopter, an end 145 of sampling tube 140 may be placed in or near the center of the runway or helicopter pad, respectively, or at an elevated position in an airspace proximate to the runway or helicopter pad (e.g., on the roof of a building proximate to an approach path).

Other embodiments, uses and advantages of the invention will be apparent to those skilled in the art from consideration of the specification and practice of the invention disclosed herein. The specification should be considered exemplary only, and the scope of the invention is accordingly intended to be limited only by the following claims.

What is claimed is:

1. A system for measuring the concentration of one or more constituents present in an exhaust plume of a vehicle traveling on a roadway, comprising:
   a trace gas detection system, located remotely from the roadway, including a measurement cell;
   a sampling tube having a first end that is positioned in the roadway, and a second end that interfaces with the measurement cell of the trace gas detection system; and
   a vacuum pump configured to draw air away from the roadway to the measurement cell of the trace gas detection system at a predetermined flow rate, through the sampling tube, such that air including a sample of an exhaust plume from a passing vehicle may be provided to the measurement cell so the concentration of one or more constituents present in the exhaust plume sample may be measured.

2. The system of claim 1, wherein the first end of the sampling tube is positioned approximately in the center of a vehicle travel lane of the roadway.

3. The system of claim 1, wherein the sampling tube comprises an inner tube disposed within a protective outer tube.

4. The system of claim 3, wherein the protective outer tube is fabricated from at least one of copper or stainless steel.

5. The system of claim 1, wherein a portion of the sampling tube proximate to the first end positioned in the roadway is secured to a surface of the roadway to maintain it in a fixed position.

6. The system of claim 1, wherein the predetermined flow rate is approximately 5.0 standard liters per minute.

7. The system of claim 1, wherein pressure in the sampling tube decreases over the length of the sampling tube from the first end positioned in the roadway to the second end that interfaces with the measurement cell of the trace gas detection system.

8. The system of claim 1, wherein pressure in the sampling tube decreases over the length of the sampling tube from atmospheric pressure at the first end to approximately 50 torr at the second end that interfaces with the measurement cell of the trace gas detection system.

9. The system of claim 1, wherein the trace gas detection system comprises a mass spectrometer.

10. The system of claim 1, wherein the trace gas detection system comprises a visible/ultraviolet absorption spectrometer.

11. The system of claim 1, wherein the trace gas detection system comprises an infrared absorption spectrometer.

12. The system of claim 1, wherein the trace gas detection system comprises a Quantum Cascade laser spectrometer, and further comprises a source and detector.

13. The system of claim 12, wherein the source comprises a thermoelectrically cooled mid-infrared quantum cascade laser.

14. The system of claim 12, wherein the detector comprises a thermoelectrically cooled mid-infrared detector.

15. The system of claim 12, wherein the measurement cell comprises an astigmatic multipass absorption cell.

16. The system of claim 1, wherein emissions from a plurality of vehicles are measured over a predetermined period of time to provide a representation of emissions attributable to general traffic.

17. The system of claim 1, wherein individual exhaust samples are associated with individual vehicles.

18. The system of claim 17, further comprising an imaging unit located proximate to the roadway to record images of passing vehicles for identification purposes.

19. The system of claim 18, further comprising a computer in operative communication with the imaging unit and the trace gas detection system, wherein the computer correlates vehicle identification information with measured emissions information.

20. The system of claim 1, further comprising a fine particle measurement system for detecting fine particulate matter present in the exhaust plume sample.

21. The system of claim 20, wherein the fine particle measurement system comprises an aerosol mass spectrometer.

22. The system of claim 20, wherein the fine particle measurement system comprises a condensation particle counter.

23. The system of claim 20, wherein the fine particle measurement system comprises a light scattering detector.

24. The system of claim 20, wherein the fine particle measurement system comprises a laser incandescent particle detector.

25. A method of measuring the concentration of one or more constituents present in an exhaust plume of a vehicle traveling on a roadway, comprising:
positioning a sampling tube such that a first end of the sampling tube is in the roadway, and a second end of the sampling tube interfaces with a measurement cell of a trace gas detection system located remotely from the roadway; and
drawing air away from the roadway to the measurement cell of the trace gas detection system, through the sampling tube, at a predetermined flow rate via a vacuum pump, such that air including a sample of an exhaust plume from a passing vehicle may be provided to the measurement cell so the concentration of one or more constituents present in the exhaust plume sample may be measured.

26. The method of claim 25, further comprising:
positioning the first end of the sampling tube approximately in the center of a vehicle travel lane of the roadway.

27. The method of claim 25, wherein the sampling tube comprises an inner tube disposed within a protective outer tube.

28. The method of claim 27, wherein the protective outer tube is fabricated from at least one of copper or stainless steel.

29. The method of claim 25, further comprising:
securing a portion of the sampling tube proximate to the first end of the sampling tube, positioned in the roadway, to a surface of the roadway to maintain it in a fixed position.

30. The method of claim 25, wherein the predetermined flow rate is approximately 5.0 standard liters per minute.

31. The method of claim 25, wherein pressure in the sampling tube decreases over the length of the sampling tube from the first end positioned in the roadway to the second end that interfaces with the measurement cell of the trace gas detection system.

32. The method of claim 25, wherein pressure in the sampling tube decreases over the length of the sampling tube from atmospheric pressure at the first end to approximately 50 torr at the second end that interfaces with the measurement cell of the trace gas detection system.

33. The method of claim 25, wherein the trace gas detection system comprises a mass spectrometer.

34. The method of claim 25, wherein the trace gas detection system comprises a visible/ultraviolet absorption spectrometer.

35. The method of claim 25, wherein the trace gas detection system comprises an infrared absorption spectrometer.

36. The method of claim 25, wherein the trace gas detection system comprises a Quantum Cascade laser spectrometer, and further comprises a source and detector.

37. The method of claim 36, wherein the source comprises a thermoelectrically cooled mid-infrared quantum cascade laser.

38. The method of claim 36, wherein the detector comprises a thermoelectrically cooled mid-infrared detector.

39. The method of claim 36, wherein the measurement cell comprises an astigmatic multipass absorption cell.

40. The method of claim 25, further comprising:
measuring emissions from a plurality of vehicles over a predetermined period of time to provide a representation of emissions attributable to general traffic.

41. The method of claim 25, further comprising:
associating individual exhaust samples with individual vehicles.

42. The method of claim 41, further comprising:
positioning an imaging unit proximate to the roadway to record images of passing vehicles for identification purposes.

43. The method of claim 42, further comprising:
correlating vehicle identification information with measured emissions information via a computer, the computer in operative communication with the imaging unit and the trace gas detection system.

44. The method of claim 25, further comprising:
providing a fine particle measurement system for detecting fine particulate matter present in the exhaust plume sample.

45. The method of claim 44, wherein the fine particle measurement system comprises an aerosol mass spectrometer.

46. The method of claim 44, wherein the fine particle measurement system comprises a condensation particle counter.

47. The method of claim 44, wherein the fine particle measurement system comprises a light scattering detector.

48. The method of claim 44, wherein the fine particle measurement system comprises a laser incandescent particle detector.

49. A system for detecting fine particulate matter present in an exhaust plume of a vehicle traveling on a roadway, comprising:
a fine particle measurement system located remotely from the roadway;
a sampling tube having a first end that is positioned in the roadway, and a second end that interfaces with the fine particle measurement system; and
a vacuum pump configured to draw air away from the roadway to the fine particle measurement system at a predetermined flow rate, through the sampling tube, such that air including a sample of an exhaust plume from a passing vehicle may be provided to the fine particle measurement system for the detection of fine particulate matter present in the exhaust plume sample.

50. A method of detecting fine particulate matter present in an exhaust plume of a vehicle traveling on a roadway, comprising:
positioning a sampling tube such that a first end of the sampling tube is in the roadway, and a second end of the sampling tube interfaces with a fine particle measurement system located remotely from the roadway; and
drawing air away from the roadway to the fine particle measurement system, through the sampling tube, at a predetermined flow rate via a vacuum pump, such that air including a sample of an exhaust plume from a passing vehicle may be provided to the fine particle measurement system for the detection of fine particulate matter present in the exhaust plume sample.

* * * * *